(12) United States Patent
Lin et al.

(10) Patent No.: US 12,198,339 B2
(45) Date of Patent: Jan. 14, 2025

(54) EVALUATION METHOD AND SYSTEM FOR CORROSION DEGREE OF ABSORBABLE STENT

(71) Applicant: BIOTYX MEDICAL (SHENZHEN) CO., LTD., Guangdong (CN)

(72) Inventors: Wenjiao Lin, Shenzhen (CN); Haifeng Li, Shenzhen (CN)

(73) Assignee: BIOTYX MEDICAL (SHENZHEN) CO., LTD., Guangdong (CN)

(*) Notice: Subject to any disclaimer, the term of this patent is extended or adjusted under 35 U.S.C. 154(b) by 385 days.

(21) Appl. No.: 17/802,467

(22) PCT Filed: May 27, 2020

(86) PCT No.: PCT/CN2020/092510
§ 371 (c)(1),
(2) Date: Aug. 25, 2022

(87) PCT Pub. No.: WO2021/135058
PCT Pub. Date: Jul. 8, 2021

(65) Prior Publication Data
US 2023/0118757 A1    Apr. 20, 2023

(30) Foreign Application Priority Data
Dec. 31, 2019 (CN) .......................... 201911407589.6

(51) Int. Cl.
*G06T 7/00* (2017.01)
(52) U.S. Cl.
CPC .. *G06T 7/0012* (2013.01); *G06T 2207/10101* (2013.01); *G06T 2207/30101* (2013.01)
(58) Field of Classification Search
None
See application file for complete search history.

(56) References Cited

U.S. PATENT DOCUMENTS

| 8,478,387 B2 | 7/2013 | Xu |
| 9,462,950 B2 | 10/2016 | Xu |

(Continued)

FOREIGN PATENT DOCUMENTS

WO    WO-2012127207 A1 *  9/2012  ......... G01N 21/8851

OTHER PUBLICATIONS

In Vitro and In Vivo Testing of Zinc as a Biodegradable Material for Stents Fabricated by Photo-Chemical Etching, By Bala Subramanya Pavan Kumar Kandala et al. Appl. Sci. 2019, 9, 4503; doi:10.3390/app9214503 (Year: 2019).*

(Continued)

*Primary Examiner* — Vikkram Bali
(74) *Attorney, Agent, or Firm* — Raymond Sun

(57) ABSTRACT

An evaluation method and system for the corrosion degree of an absorbable stent. The method includes the following steps: obtaining the total number $S_0$ of stent bars of the absorbable stent at the time zero of implantation (S10); separately obtaining n frames of optical coherence tomography (OCT) images of the absorbable stent at the time x of implantation, wherein x is greater than 0, and n is a natural number greater than 1 (S20); determining, according to the n frames of OCT images, the total number Ni of the stent bars corresponding to each frame of OCT image, wherein i is a natural number greater than or equal to 1 and less than or equal to n; and calculating the total number $S_x$ of the stent bars corresponding to the n frames of OCT images at the time x of implantation (I) (S30); determining a corrosion degree Cij of a jth stent bar in an ith frame of OCT image at the time x of implantation, wherein j is a natural number greater than or equal to 1 and less than or equal to Ni (S40); and calculating an overall corrosion degree Cx of the absorbable stent at the time x of implantation according to (Continued)

the following formula: (II) (S50). The evaluation method can be applied to clinical treatment.

13 Claims, 9 Drawing Sheets

(56) References Cited

U.S. PATENT DOCUMENTS

| | | |
|---|---|---|
| 10,335,039 B2 | 7/2019 | Xu |
| 2010/0094127 A1* | 4/2010 | Xu .................. G06F 18/24 600/425 |
| 2012/0002855 A1 | 1/2012 | Bai |
| 2014/0076719 A1* | 3/2014 | Andreacchi .............. C25F 7/00 204/198 |

OTHER PUBLICATIONS

Design and characterization of a novel biocorrodible iron-based drug-eluting coronary scaffold, by Wen-Jiao Lin et al., Materials and Design 91 (2016) 72-79 (Year: 2016).*

Search Report for Corresponding PCT Application No. PCT/CN2020/092510.

* cited by examiner (f)　　　(g)　　　(h)

EVALUATION METHOD AND SYSTEM FOR CORROSION DEGREE OF ABSORBABLE STENT

TECHNICAL FIELD

The present invention relates to the technical field of medical imaging, and in particular to an evaluation method and system for the corrosion degree of an absorbable stent.

BACKGROUND ART

This section provides only background information related to the present invention, which is not necessarily the existing art.

Coronary atherosclerotic heart disease, or coronary heart disease for short, is one of the leading causes of death worldwide. At present, a therapy for the coronary heart disease mainly adopts percutaneous coronary intervention; that is, a stent is used to reconstruct a blood vessel. The first generation of stents was a bare metal stent (BMS), which had the disadvantage of high postoperative vascular restenosis rate. The second generation of stent was a drug-eluting stent (DES), which significantly reduced the restenosis rate of a blood vessel, but causes poor late stent adherence, thus leading to thrombosis. The third generation of stent was a biological resorbable stent (BRS), which can provide temporary radial strength and avoid acute retraction of a blood vessel. After a period of time from the implantation, the stent would be completely absorbed, thereby completing vascular remodeling and restoring blood supply. With the development of technology, the BRS has been used more and more widely used.

However, existing studies have shown that patients may suffer from in-stent restenosis (ISR) due to vascular damage, inflammatory reaction and other factors after interventional treatment for the coronary heart disease with an absorbable stent.

When ISR occurs in a stent segment, a doctor generally considers re-implantation of a new stent for revascularization again. However, if the previously implanted absorbable stent is still not corroded (or degraded) or its corrosion degree (or degradation) is very low, the absorbable stent is still bound to the blood vessel, and the doctor may not be able to implant a new stent for expansion. The ISR can only be treated with more invasive surgery. Therefore, when ISR occurs, evaluation of the corrosion degree (or degradation) of the absorbable stent in vivo is crucial to assist a doctor in evaluating which method can be used for revascularization.

Considering that the corrosion rates (or degradation rates) of stents in different patients or even in different parts of the same patient are greatly different, the corrosion degree (or degradation degree) needs to be evaluated separately for each stent. Currently, a weight loss method is generally used to evaluate a corrosion degree (or degradation degree) of a stent. In this method, a calculation formula for a corrosion degree of a stent is: $C_{weight\ loss}=(a-b)/a$, where a is a mass of the stent before implantation; b is a remaining mass of the stent after corrosion or degradation; and a numerical value of a can be measured before implantation. For a numerical value of b, after the stent is taken out from the body, a tissue is first dissolved, and then the remaining mass of the stent is measured. The remaining mass is the numerical value of b. The weight loss method can more accurately evaluate the corrosion degree of the stent, but in this method, tissues around the stent need to be taken out of the body when the stent is taken out. Therefore, this method cannot be used clinically and can only be used in animal experiments. In the prior art, there is currently no method for accurately, quantitatively or semi-quantitatively, evaluating the corrosion degree of an absorbable stent in clinical practice.

SUMMARY OF THE INVENTION

Based on this, it is necessary to provide an evaluation method and system for the corrosion degree of an absorbable stent in clinical practice.

An evaluation method for the corrosion degree of an absorbable stent includes the following steps:
  obtaining the total number $S_0$ of stent bars of the absorbable stent at the time zero of implantation;
  separately obtaining n frames of optical coherence tomography (OCT) images of the absorbable stent at the time x of implantation, wherein x is greater than 0, and n is a natural number greater than 1;
  determining, according to the n frames of OCT images, the total number Ni of the stent bars corresponding to each frame of OCT image, wherein i is a natural number greater than or equal to 1 and less than or equal to n; and calculating the total number Sx of the stent bars corresponding to the n frames of OCT images at the time x of implantation, $$Sx = \sum_{i=1}^{n} Ni;$$

determining a corrosion degree Cij of a jth stent bar in an ith frame of OCT image at the time x of implantation, wherein j is a natural number greater than or equal to 1 and less than or equal to Ni; and
  calculating an overall corrosion degree Cx of the absorbable stent at the time x of implantation according to the following formula:

$$Cx = \left( \frac{\sum_{i=1}^{n}\sum_{j=1}^{Ni} Cij}{S_0} + \frac{S_0 - S_x}{S_0} \right) \times 100\%.$$

In one embodiment, each frame of OCT image refers to an OCT image of each section of the absorbable stent that is perpendicular to an axial central axis.

In one embodiment, the absorbable stent includes h wave loops arranged along an axial direction, with $n \geq h$.

In one embodiment, an axial distance between sections corresponding to any two adjacent frames is equal.

In one embodiment, the corrosion degree Cij at least includes no corrosion, partial corrosion, and full corrosion; Cij corresponding to no corrosion is 0%; Cij corresponding to partial corrosion is 50%; and Cij corresponding to full corrosion is 100%.

In one embodiment, the total number Ni of the stent bars refers to a sum of the numbers of stent bars that simultaneously satisfy the following two conditions:
  (1) in an OCT image, the brightness of a stent bar is higher than that of a surrounding tissue; and
  (2) in an OCT image, a stent bar has a black tail shadow.

In one embodiment, the corrosion degree Cij at least includes no corrosion, preliminary corrosion, partial corrosion, and full corrosion; Cij corresponding to no corrosion is 0%; Cij corresponding to preliminary corrosion is 20%; Cij corresponding to partial corrosion is 50%; and Cij corresponding to full corrosion is 100%.

In one embodiment, at the time zero of implantation, a contour thickness of each stent bar is $T_0$ or in a natural state, a thickness of each stent bar is $T_0$; and when the contour thickness of the stent bar is $T_1$, if $T_1$ is approximately equal to $T_0$, it is determined that the corrosion degree Cij is 0%.

In one embodiment, at the time zero of implantation, a contour thickness of each stent bar is $T_0$ or in a natural state, a thickness of each stent bar is $T_0$; and when the contour of the stent bar is an arch which has a radial height of $T_2$, if $T_2$ is approximately equal to $2T_0$, it is determined that the corrosion degree Cij is 20%.

In one embodiment, at the time zero of implantation, a contour thickness of each stent bar is $T_0$ or in a natural state, a thickness of each stent bar is $T_0$; and when the contour of the stent bar is an arch which has a radial height of $T_2$, if $T_2$ is approximately equal to $3T_0$, it is determined that the corrosion degree Cij is 50%.

In one embodiment, at the time zero of implantation, a contour thickness of each stent bar is $T_0$ or in a natural state, a thickness of each stent bar is $T_0$; and when the contour of the stent bar is an arch which has a radial height of $T_2$, if $T_2$ is greater than or equal to $4T_0$, it is determined that the corrosion degree Cij is 100%; or, when the stent bars are irregularly connected into one piece, it is determined that the corrosion degree Cij is 100%.

In one embodiment, for the absorbable stents of the same specification or for the same absorbable stent, the total number $S_0$ of the stent bars of the absorbable stent at the time zero of implantation is a constant; and the method for obtaining $S_0$ includes: obtaining n frames of OCT images of the absorbable stent at the time zero of implantation, and determining the total number $S_0$ of stent bars of the absorbable stent at the time zero of implantation according to the n frames of OCT images of the absorbable stent at the time zero of implantation.

An evaluation system for determining the corrosion degree of an absorbable stent includes:
   an OCT image obtaining module, configured to obtain n frames of OCT images of the absorbable stent;
   an OCT image identification module, configured to identify stent bars in each frame of OCT image, and calculate the total number Ni of the stent bars corresponding to each frame of OCT image and the total number Sx of the stent bars corresponding to the n frames of OCT images, $$Sx = \sum_{i=1}^{n} Ni;$$

an OCT image analysis module, configured to analyze a corrosion degree Cij of the stent bars in each frame of OCT image; and
   a calculation module, configured to calculate an overall corrosion degree Cx of the absorbable stent according to a formula $$Cx = \left( \frac{\sum_{i=1}^{n}\sum_{j=1}^{Ni} Cij}{S_0} + \frac{S_0 - S_x}{S_0} \right) \times 100\%.$$

In the above-mentioned evaluation method for the corrosion degree of an absorbable stent, OCT is used for in-vivo tomography. Corrosion degrees of a plurality of stent bars are determined through OCT images, and the corrosion degrees of the plurality of stent bars are averaged and corrected to obtain a corrosion degree of the absorbable stent at certain time after implantation. An experiment shows that the method can accurately evaluate, quantitatively or semi-quantitatively, a corrosion degree of an absorbable stent, so that the method can be applied clinically.

DETAILED DESCRIPTION OF THE INVENTION

In order to make the foregoing objectives, features and advantages of the present invention more obvious and understandable, the specific implementation modes of the present invention are described in detail with reference to the accompanying drawings. Many specific details are described in the following descriptions to facilitate full understanding of the present invention. However, the present invention can be implemented in a variety of other ways than those described herein, and those skilled in the art can make similar improvements without departing from the connotation of the present invention. Therefore, the present invention is not limited by specific implementations disclosed below.

Unless otherwise defined, all technical and scientific terms used herein are the same as meanings of general understandings of those skilled in the art of the disclosure. The terms used in the description of the disclosure herein are merely to describe the specific embodiments, not intended to limit the disclosure.

In the field of interventional medical apparatuses, "distal end" is defined as an end far from an operator during surgery, and "proximal end" is defined as an end close to the operator during surgery. "Axial direction" refers to a direction parallel to a connecting line between a center of a distal end of a medical apparatus and a center of a proximal end, and "radial direction" refers to a direction perpendicular to the above axial direction.

Figure 1:
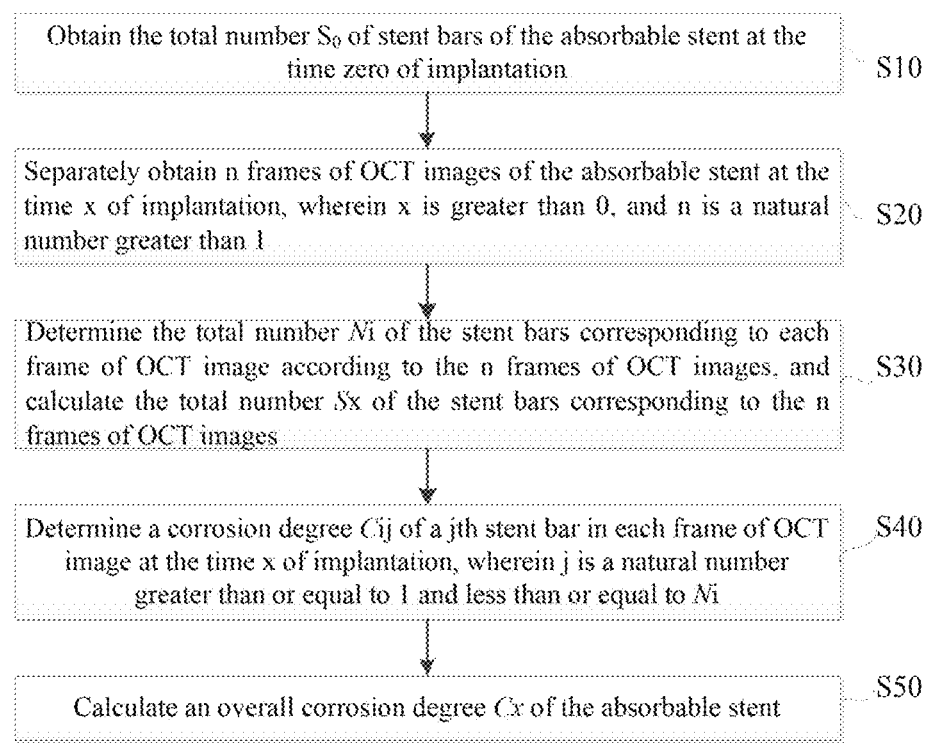
FIG. 1 is a flowchart of an evaluation method for the corrosion degree of an absorbable stent according to one implementation.

Referring to FIG. 1, an evaluation method for the corrosion degree of an absorbable stent according to one embodiment includes the following steps S10-S50.

S10: the total number $S_0$ of stent bars of an absorbable stent at the time zero of implantation is obtained.

The absorbable stent refers to an absorbable lumen stent, which includes a plurality of stent bars.

The time zero of implantation is the time when implantation is just completed. At this time, the corrosion state (an intact state) of the absorbable stent is consistent with the corrosion state of the absorbable stent before implantation. Therefore, the total number $S_0$ of the stent bars of the absorbable stent at the time zero of implantation is equal to the total number $S_0$ of the stent bars of the absorbable stent before implantation. That is, $S_0$ is a sum of the numbers of stent bars of various sections of the absorbable stent in a natural state.

For the absorbable stents of the same specification or for the same absorbable stent, $S_0$ is a constant.

In one implementation mode, in order to ensure the consistency of data or to reduce an error as much as possible, $S_0$ is obtained at the time zero of implantation through the following method:

obtaining n frames of OCT images of the absorbable stent at the time zero of implantation, and determining the total number $S_0$ of the stent bars of the absorbable stent at the time zero of implantation according to the n frames of OCT images of the absorbable stent at the time zero of implantation, wherein n is a natural number greater than 1.

In one implementation, in an OCT image, the width of a stent bar at a wave head position (i.e., a wave crest or wave trough position in a wave loop structure) of the stent is two or three times that of a normal stent bar image, so that in order to avoid excessive corrosion caused by a small number of stent bars, one stent bar at the wave head position needs to be calculated as two or three bars. In the OCT image, an image of the wave head position of the stent is longer than a wave rod, so that a wave head and a wave rod can be distinguished.

S20: n frames of OCT images of the absorbable stent at the time x of implantation are separately obtained, wherein x is greater than 0, and n is a natural number greater than 1.

The time x of implantation refers to any time after implantation except the time zero of implantation. For example, it is 1 month of implantation, 3 months of implantation, 6 months of implantation, 12 months of implantation, 24 months of implantation, 36 months of implantation, or 48 months of implantation. The time x of implantation may be determined according to clinical follow-up time or determined according to an actual need.

OCT refers to Optical Coherence Tomography, which is new tomography, is an optical imaging technology, that avoids potential harms caused by X ray, a high-intensity magnetic field, ultrasonic waves and other radiations to people, and providing a safe monitoring means. In addition, the OCT can carry out in-vivo tomography. An OCT image of the absorbable stent in vivo at the time i of implantation is directly collected to analyze the corrosion degree of the absorbable stent, so that the defect that a weight loss method cannot be applied to clinical analysis can be avoided. Furthermore, in the OCT, through the use of the characteristics of high light intensity and low single-pulse energy of an ultrafast laser, injury to a tissue can be avoided, and quick imaging can also be achieved; a high space resolution and a large detection depth are obtained; the safety is good, and the accuracy is high.

S30: the total number Ni of stent bars corresponding to each frame of OCT image is separately determined according to the n frames of OCT images, and the total number Sx of stent bars corresponding to the n frames of OCT images is calculated, $$Sx = \sum_{i=1}^{n} Ni;$$

The n frames of OCT images in S20 and S30 refer to OCT images of n sections of the absorbable stent. The sections are sections of the absorbable stent that are perpendicular to an axial central axis. Each frame of OCT image corresponds to one section. One frame is a two-dimensional vascular cross section, and the cross sections are superimposed into a three-dimensional OCT image. After the absorbable stent is scanned using OCT, a plurality of stent cross section images that respectively display the stent bars will be obtained.

Ni is the total number of stent bars of an ith frame, and i is a natural number greater than or equal to 1 and less than or equal to n.

In one implementation, in the OCT scanning process, the number of frames is constant according to a set parameter. Each frame in the OCT image of the absorbable stent at the time zero of implantation and the time i of implantation can be separately analyzed. By this analysis method, when each stent bar in each frame is analyzed, obtained data is the most accurate, but there is a large amount of data, so that evaluation takes a lot of time.

In one implementation, in order to save time and improve the efficiency, the treatment can also be simplified. One frame is selected for analysis every y frames, where y is a non-zero natural number such as 1, 2, 3, and 4. Alternatively, any frame is selected from every z frames for evaluation, where z is a non-zero natural number. In such a treatment mode, among the plurality of selected frames to be analyzed, an axial distance between the sections corresponding to any two adjacent frames is equal. By means of uniformly selecting points, the evaluation time is manyfold reduced, and the same accurate result is achieved.

It should be noted that the frames in S20 and S30 are frames for analysis, which may be all collected frames, or may be part of the collected frames.

In one implementation, an axial length of the absorbable stent corresponding to every 5 or 10 continuous frames is 1 mm.

In one implementation, a plurality of sections of the absorbable stent are selected according to a desired gap, and a plurality of frames of OCT images are correspondingly collected. That is, the number of frames of OCT images is determined according to the number of sections to be evaluated, so as to improve the efficiency. For example, one frame of OCT image can be collected according to a gap of 0.02 mm, 0.01 mm and 0.005 mm. It should be noted that the number of section frames at the time zero of implantation should be consistent with the number of section frames at the follow-up time.

In one implementation, the absorbable stent includes h wave loops arranged along an axial direction, and the number n of frames to be analyzed is greater than or equal to h. That is, the number of frames to be analyzed is at least equal to the number h of the wave loops, so that the stent bars of each wave loop are analyzed to ensure the accuracy of analysis results.

Figure 2:
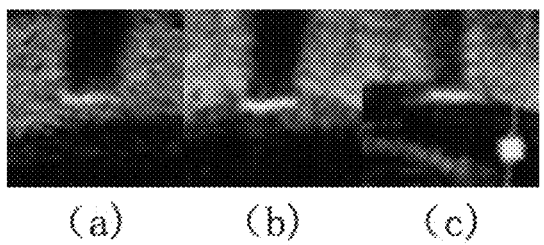
FIG. 2 is an OCT image of an uncorroded state.

According to the action mechanism of the OCT, near infrared ray emitted by an OCT catheter light source reaches a human tissue through an optical fiber and a probe. Optical waves backscattered by the tissue are collected by the probe and form interference together with an optical wave signal of a reference arm; and a high-definition image that shows an internal microscopic structure of a sample to be analyzed is constructed via computer analysis. The brightness in an image is related to an optical density of this substance. A part with higher brightness has a larger optical density. The optical density of a metal is much higher than that of blood or that of a vascular wall tissue, so that the stent bar has higher brightness. The part with higher brightness as shown in FIG. 2 is a stent bar. Furthermore, since blood and a vascular wall tissue in a blood vessel are relatively loose, OCT optical waves can penetrate through them, while a stent bar is made of a dense metal material, and OCT optical waves cannot penetrate through them. Therefore, the OCT optical waves should be completely reflected on the stent bars. In view of the images, the optical wave is a long black tail shadow, such as a black strip region corresponding to the part with higher brightness shown in FIG. 2.

Therefore, the stent bars analyzed simultaneously satisfy the following two conditions:

(1) in an OCT image, the brightness of a stent bar is higher than that of a surrounding tissue; and (2) in an OCT image, a stent bar has a black tail shadow.

In condition (1), it can be identified with equipment or human eyes that the brightness of the stent bar is higher than the brightness of other regions.

The total number of the stent bars per frame to be analyzed is the total number $N_i$ of stent bars per frame.

S40: the corrosion degree $C_{ij}$ of a jth stent bar in each frame of OCT image at the time x of implantation is determined, wherein j is a natural number greater than or equal to 1 and less than or equal to $N_i$.

On the premise of ensuring the accuracy, in order to simplify a model, in one implementation, the corrosion degree of the stent bar is at least divided into three kinds: no corrosion, partial corrosion and full corrosion. $C_{ij}$ corresponding to no corrosion is 0%; $C_{ij}$ corresponding to partial corrosion is 50%; and $C_{ij}$ corresponding to full corrosion is 100%.

A determination criterion for the corrosion degree of a stent bar is established first. The determination criterion is established according to the following method.

Figure 3:
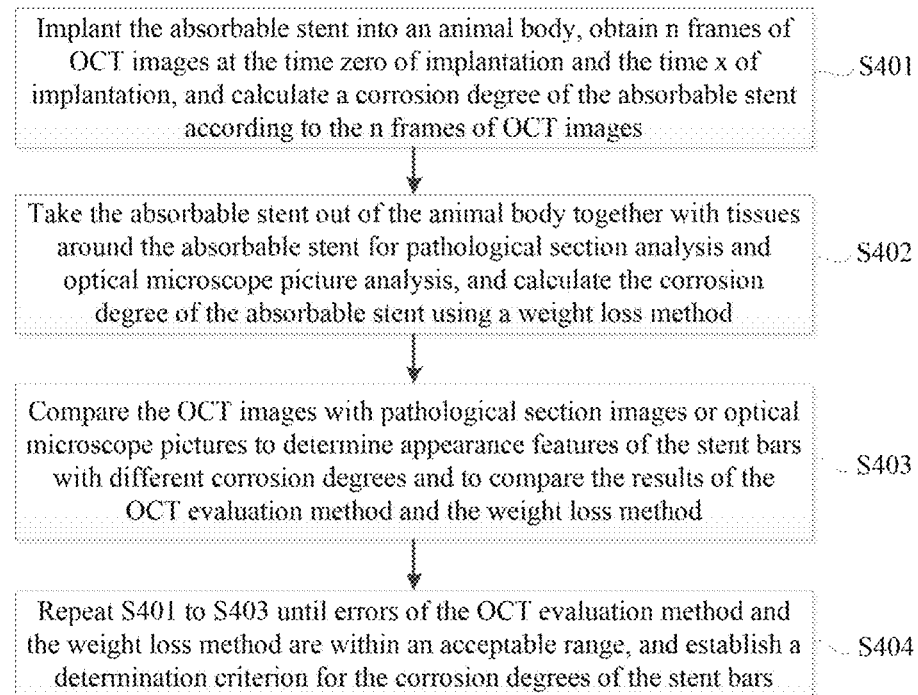
FIG. 3 is a flowchart of a method for establishing a determination criterion for the corrosion degree of a stent bar according to one implementation.

As shown in FIG. 3, the method for establishing the determination criterion includes the following steps:

S401: the absorbable stent is implanted into an animal body; n frames of OCT images at the time zero of implantation and the time x of implantation are obtained; and the corrosion degree of the absorbable stent is calculated according to the n frames of OCT images.

The calculation mode for calculating the corrosion degree of the absorbable stent according to the OCT image refers to the step S50.

S402: the absorbable stent is taken out of the animal body together with tissues around the absorbable stent for pathological section analysis and optical microscope picture analysis, and the corrosion degree of the absorbable stent is calculated using the weight loss method.

S403: the OCT images are compared with pathological section images or optical microscope pictures to determine appearance features of the stent bars with different corrosion degrees and to compare the results of the OCT evaluation method and the weight loss method.

S404: S401 to S403 are repeated until errors of the OCT evaluation method and the weight loss method are within an acceptable range, and a determination criterion for the corrosion degrees of the stent bars is established.

Through an animal experiment, OCT images at the corresponding time points (such as the time x of implantation), and appearance features of uncorroded, partially corroded, and fully corroded stent bars under an optical microscope and pathology are obtained.

A specific experimental method is as follows: multiple absorbable stents are respectively implanted into the bodies of multiple rabbits, and OCT images are obtained immediately after implantation; the absorbent stents that are implanted into the bodies at different time points are separately scanned using OCT, such as 12 months, 24 months, 36 months, and 48 months; and after the OCT images at the corresponding time points are obtained, vascular tissues with the absorbable stents are taken out of the animal bodies to observe the appearances of the stent bars of the absorbable stents under an optical microscope and pathology. After completion, the tissues are ablated, and then corrosion degrees C1 of the absorbable stents are tested using the weight loss method. A preliminary corrosion degree evaluation criterion is set according to the corrosion degrees C1 of different stents and the appearance features of the corresponding stent bars. The existing OCT images are analyzed according to the corrosion degree evaluation criterion, so as to evaluate an overall corrosion degree C2 of each stent. The evaluation criterion for the appearance features of the stent bars with different corrosion degrees in the OCT images is continuously optimized and adjusted according to an error between C1 and C2.

Through multiple cyclic tests, a set of relatively accurate evaluation criterion is finally obtained, which is shown in Table 1 below.

TABLE 1

| Corrosion degree | Feature |
| --- | --- |
| No corrosion | 1. An uncorroded stent bar satisfies all features of a basic form of a stent bar.<br>2. The contour of the stent bar with high brightness satisfies the following graphic features:<br>a quadrangle (as shown in (a) of FIG. 2), an approximate quadrangle, and a crescent shape (the center of the crescent points to the OCT catheter, as shown in (c) of FIG. 2), the contour of which is as shown below:<br>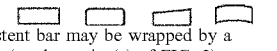<br>The stent bar may be wrapped by a tissue (as shown in (a) of FIG. 2), or may be exposed from the tissue (as shown in (c) of FIG. 2).<br>3. The contour thickness satisfies 70% D ≤ $D_0$ ≤ 130% D: D is an original stent bar thickness (a theoretical value), and $D_0$ is the contour thickness of the stent bar (as shown in (b) of FIG. 2, the width of the rectangle). An error is considered to be 30%. |
| Partial corrosion | A partially corroded stent bar only needs to satisfy one of the following conditions:<br>1. The partially corroded stent bar satisfies all features of a basic form of a stent bar:<br>The contour of the stent bar with high brightness satisfies the following graphic features:<br>a quadrangle, an approximate quadrangle, and a crescent shape (the |

TABLE 1-continued

Figure 4:
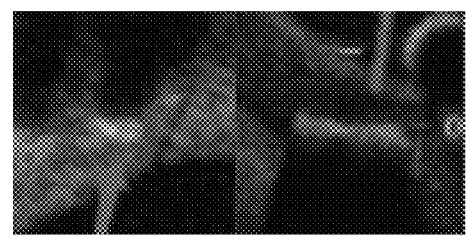
FIG. 4 is an OCT image of a partially corroded state.
Figure 5:
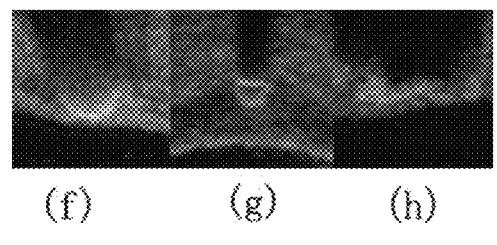
FIG. 5 is an OCT image of a fully corroded state.

| Corrosion degree | Feature |
|---|---|
| | center of the crescent points to the OCT catheter), the contour of which is as shown below:  The stent bar may be wrapped by a tissue, or may be exposed from the tissue. The contour thickness DI satisfies D1 > 130% D, as shown in (d) and (e) of FIG. 4. 2. The partially corroded stent bar satisfies all the features of a basic form of a stent bar, but is quite different from the features of uncorroded and fully corroded stent bars. |
| Full corrosion | A fully corroded stent bar only needs to satisfy one of the following conditions: 1. The fully corroded stent bar satisfies a basic form of a stent bar and is wrapped by a tissue, but its contour is roughly circular (as shown in (f) of FIG. 5), formless (in an irregular form) (as shown in (h) of FIG. 5) and the like. 2. The fully corroded stent bar satisfies a basic form of a stent bar, is wrapped by a tissue, and is internally hollow (as shown in (g) of FIG. 5). |

The time zero of implantation is immediately after implantation. At this time, since the stent has just been implanted, the stent bars are not corroded. Therefore, the stent bars in the OCT images at the time zero of implantation should be the uncorroded stent bars. It can be set that the corrosion degree of the uncorroded stent bar is 0%, and its appearance feature can be used as the appearance feature of the uncorroded stent bar. The appearance feature of the uncorroded stent bar is more obvious and objective, but considering errors of OCT equipment and in a surgical process, as well as an evaluation error in the evaluation process, errors of the three kinds of corrosion degrees are all set to be ±25%. Since there is no minus for the corrosion degree, that is, the corrosion degree in the uncorroded state is 0-25%.

According to the above, the part with high brightness in the OCT image is a stent bar, so the edge of the part with high brightness can be drawn as a contour to describe the form of the stent bar. In the existing stent, the stent bar is generally prepared by cutting a metal tube with laser and polishing or etching the cut metal tube, so the cross section of the stent bar is generally quadrilateral, and the quadrangle may have rounded corners or may not have rounded corners. In addition, since the stent is bound by a blood vessel after expansion, the stent bar may be flush with a vascular wall. From the cross section, the stent bar is shaped like a crescent, but the center of the crescent should point to an OCT catheter at this time, as shown in (a), (b) and (c) in FIG. 2.

In the uncorroded state, the contour thickness of the stent bar is the same as that before implantation. If a theoretical value of an original stent bar thickness is set to be D, when an OCT measurement error is relatively large, an error bar is set to be ±30%, and the contour thickness Do of the stent bar is within a range of 70% $D \leq D_0 \leq 130\%$ D.

In the partially corroded state, that is, when the stent bar has been corroded, but is not fully corroded, its corrosion degree is set to be 50±25%. At this time, the stent bar is still basically intact, and its appearance feature is basically the same as that in the uncorroded state; and the stent bar is still internally dense. Ionic corrosion products formed after corrosion can be dissolved in a body fluid and absorbed by a human body. A solid corrosion product formed after the stent bar is corroded is transported to an outer surface of the stent bar with the help of macrophages. Since the solid corrosion product is relatively fluffy, the OCT optical waves can penetrate through part of the solid corrosion product, so in the OCT image, the form of the partially corroded stent bar still remains intact, but the contour thickness of the stent bar is increased due to the attachment of the solid corrosion product to the outer surface of the stent bar. Therefore, the contour thickness of the partially corroded stent bar is set to be D1 which satisfies D1>130% D, as shown in (d) and (e) of FIG. 4.

When the stent has been fully corroded, the corrosion degree is 100%. However, since the corrosion degree may not exceed 100%, the corrosion degree of a full corrosion is 75 to 100%. In the fully corroded state, the metal in the original stent bar is completely transformed into corrosion products, and the stent bar no longer maintains its original form, but is replaced by a fluffy solid corrosion product. From the contour drawn by the part with high brightness, the stent bar is more like a circle or in a formless state (any irregular form). At the same time, the solid corrosion products are randomly distributed, so that the thickness of the stent bar cannot be evaluated. The scattered solid corrosion products may also be absorbed by the human body, resulting in a significantly smaller thickness of the stent bar in the OCT image, or even an unrecognizable stent bar.

The errors in the uncorroded, partially corroded, and fully corroded states are set at +25%, ±25%, and −25%, respectively, which are within an acceptable range for clinical evaluation of a corrosion degree. From pathology results, the metal part in the middle of the stent bar is often transported into a tissue by a tissue, resulting in some metal still remaining outside the stent bar, but the middle has been filled with the tissue, so from the image point of view, the stent bar is hollow. At this time, the stent bar has no supporting force, and only a shell remains. In this case, the stent bar at this time is considered to be in the fully corroded state, as shown in (f), (g) and (h) of FIG. 5. A fully corroded stent bar is significantly different from an uncorroded stent bar, and its appearance feature is also more objective.

Since the set appearance feature is relatively broad, all possibilities cannot be exhausted. In an optimal iteration process, it is found that there are some stent bars that still cannot satisfy all the stent bar features described above. Considering that the appearance features of the uncorroded and fully corroded stent bars are more objective, and the appearance feature of the partially corroded stent is located between the above two appearance features, it is difficult to completely exhaust all the features that exist as much as possible. Therefore, a new condition is added to solve this problem on the basis of the above conditions, so as to solve this problem and improve the accuracy. When a certain stent bar satisfies all the features of a basic form of a stent bar, but is quite different from the features of uncorroded and fully corroded stent bars, the corrosion degree of the stent bar is determined to be partial corrosion.

It should be noted that due to the endothelialization of a living body, the OCT images show that most of the stent bars had been wrapped by tissues during follow-up testing, and a few of stent bars are still exposed outside the tissues. Both the uncorroded and partially corroded stent bars may be possibly in the above two states. For the fully corroded stent bars, there are many solid corrosion products due to full corrosion, which stimulates the endothelialization nearby. The fully corroded stent bars are special, which have been all wrapped by tissues.

In another embodiment, the corrosion degree Cij also includes preliminary corrosion and deep corrosion. The preliminary corrosion is between no corrosion and partial corrosion, and deep corrosion is between partial corrosion and full corrosion. In one implementation, Cij of the preliminary corrosion may be 30%-35%, and Cij of the deep corrosion may be 60%-65%.

Figure 6A:
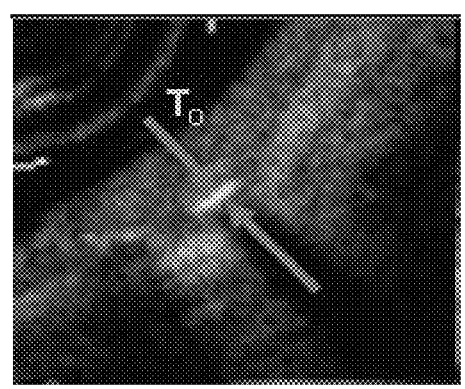
FIGS. 6a to 6j are OCT images of different corroded states.

In another embodiment, the corrosion degree of the stent bar is at least divided into the following four kinds:

(1) No corrosion: The corrosion degree Cij immediately after the stent is implanted is 0%. At this time, the contour of the stent bar is roughly quadrilateral, crescent-shaped, etc., as shown in FIG. 2 and FIG. 6a. At this time, the appearance feature of the stent bar is the same as the first and second features in the uncorroded state in Table 1 above. The contour thickness of the stent bar is $T_0$ which is a contour thickness of the stent bar measured by OCT imaging equipment at the time zero after the stent is implanted (immediately after implantation). Considering that there may be a deviation between the contour thickness of the stent bar measured by the OCT imaging equipment and the thickness of the stent bar in the natural state, the value $T_0$ measured by the OCT imaging equipment is used as a comparison reference to ensure the accuracy.

Figure 6B:
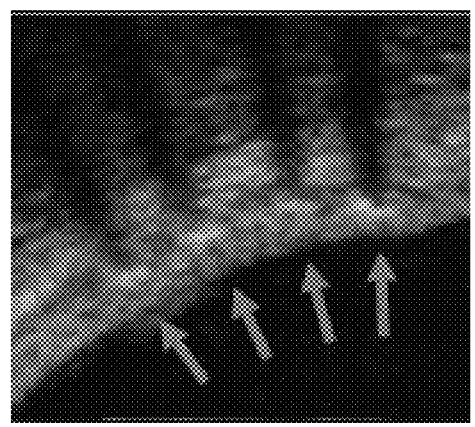
Figure 6C:

(2) No corrosion: The stent is wrapped by neointima for a period of time after implantation, but has not yet begun to be corroded. In the OCT image, the stent bar is slightly deformed or darkened. The slight deformation of the stent bar means that the contour shape of the stent bar in the OCT image is roughly the same as that of the stent bar at the time zero of implantation, as shown in FIGS. 6b and 6c. Moreover, at this time, the contour thickness of the stent bar measured by the OCT imaging equipment is $T_1$, $T_1 \approx T_0$, where "$\approx$" is determined by rounding. The corrosion degree Cij at this time is set to be 0%.

Figure 6D:
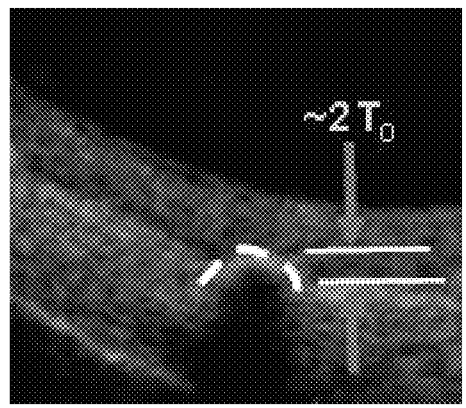
Figure 6E:
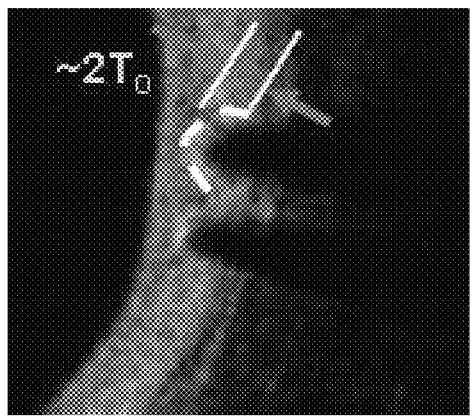

(3) Preliminary corrosion: As the implantation time increases, the corrosion degree of the stent gradually increases. In the OCT image, the stent bar expands and bulges outwardly (the direction of the bulge is away from the OCT catheter), and the contour shape of the stent bar is slightly arched, as shown in FIG. 6d and FIG. 6e. In addition, the radial height $T_2$ of the arch satisfies: $T_2 \approx 2T_0$, where "$\approx$" is determined by rounding. The corrosion degree Cij at this time is set to be 20%.

Figure 6F:
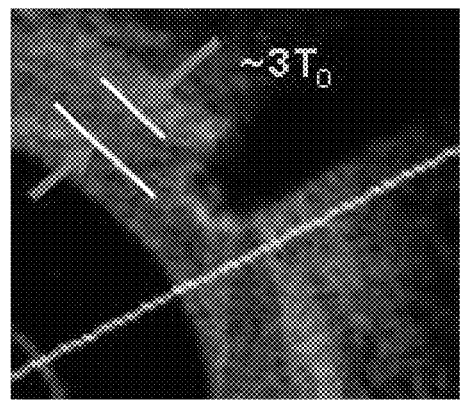
Figure 6G:
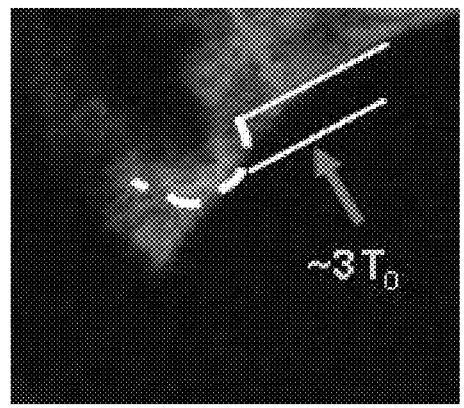

(4) Partial corrosion: As the implantation time further increases, in the OCT image, the stent bar continues to expand, the brightness of the stent bar becomes lower, and the radial height of the arch increases, as shown in FIG. 6f and FIG. 6g. In addition, the radial height $T_2$ of the arch satisfies: $T_2 \approx 3T_0$, where is determined by rounding. The corrosion degree Cij at this time is set to be 50%.

Figure 6H:
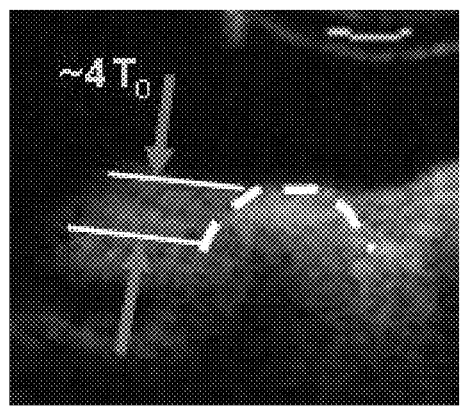
Figure 6I:
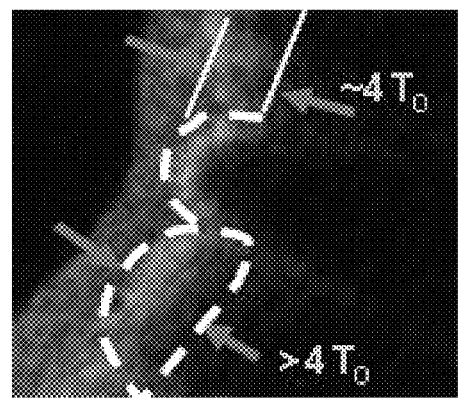
Figure 6J:

(5) Full corrosion: As the implantation time continues to increase, in the OCT image, the stent bar further expands; the contour of the arch part becomes significantly large; the radial height further increases, as shown in FIG. 6h and FIG. 6i. In addition, the radial height $T_2$ of the arch satisfies: $T_2 \geq 4T_0$. The corrosion degree Cij at this time is set to be 100%, that is, full corrosion. Alternatively, in the OCT image, no light spots with roughly quadrilateral and crescent-shaped contours can be seen, and no arch can be seen, either, but an irregular, dark form is shown, as shown in FIG. 6j. The corrosion degree Cij in this state is also set to 100%.

Figure 7:
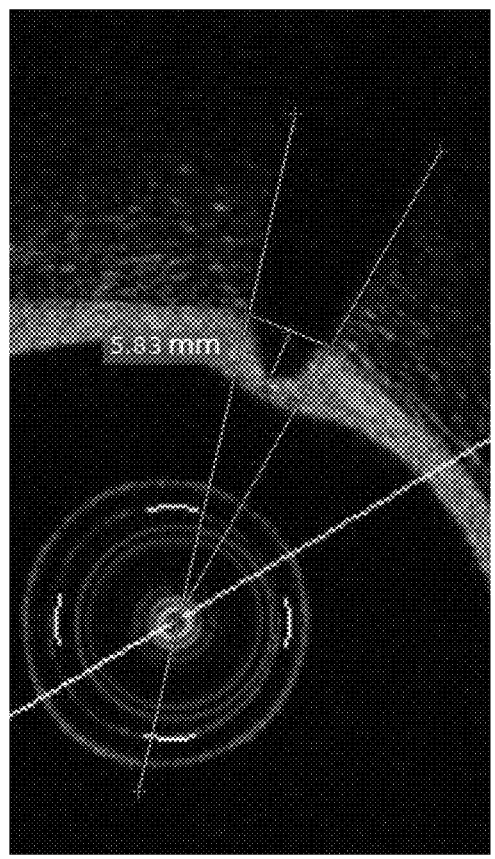
FIG. 7 is a schematic diagram of a method for calculating a radial height of an arch structure in an OCT image according to one embodiment.

It should be noted that the radial height of the arch mentioned above refers to a distance between a tangent to a closed end of the arch and a straight line passing through two end points of an opening of the arch. The radial height of the arch is measured by the OCT equipment. The measurement method is shown in FIG. 7. Among beam rays initiated by a center of the OCT catheter, two beam rays pass through two end points of an open end of the arch (an end where a tail shadow is located), that is, the two beam rays are respectively tangent to the tail shadow. Points of tangency are the two end points of the open end of the arch. A connecting line of the two end points, the two beam rays and the tangent to the closed end of the arch form a trapezoid, and the connecting line of the two end points serves as a lower bottom edge of the trapezoid; the tangent to the closed end of the arch serves as an upper bottom edge; and a height of the trapezoid is the radial height of the arch.

It should be noted that the establishing method for determining the corrosion degree Cij in this embodiment can be determined according to the above steps S401 to 404, and the above determination criterion including at least 5 corrosion degrees Cij is obtained through multiple cycle experiments. Meanwhile, when a value of T ($T_1$ and $T_2$) of a cross section of a certain bar actually measured by OCT is between the two criteria, it can be rounded to find the corresponding corrosion degree, or linear interpolation can be performed between the two criteria to obtain corresponding corrosion results for more accurate test results.

Figure 8A:
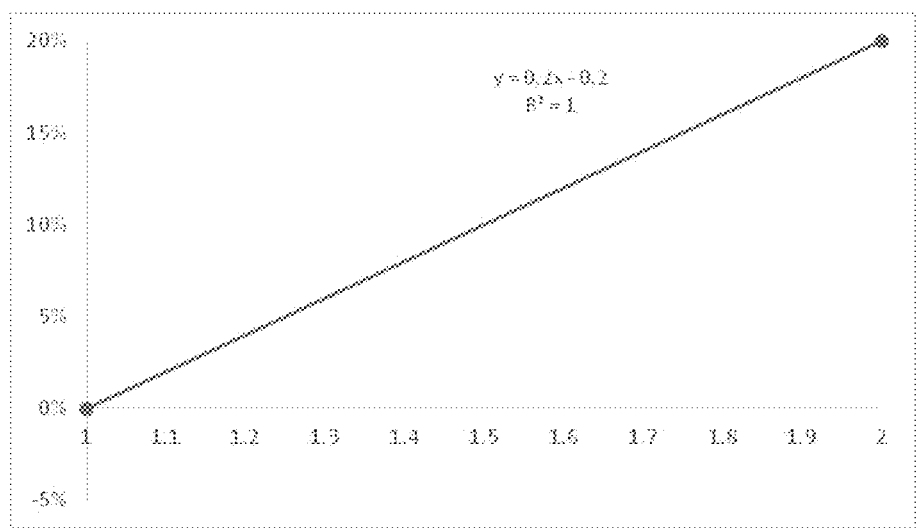
FIGS. 8(a) to 8(d) are linear relationship diagrams of corrosion degrees, contour thicknesses of stent bars, and radial heights of arch structures according to one embodiment.
Figure 8B:
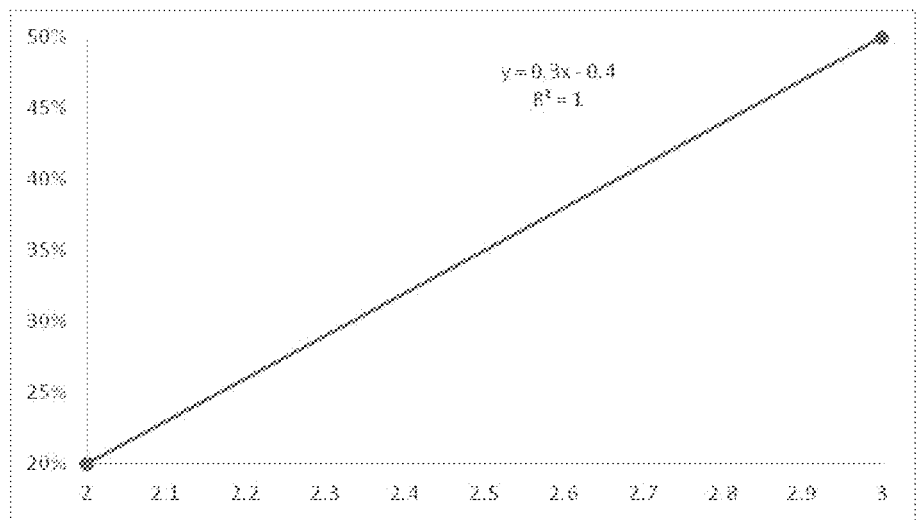
Figure 8C:
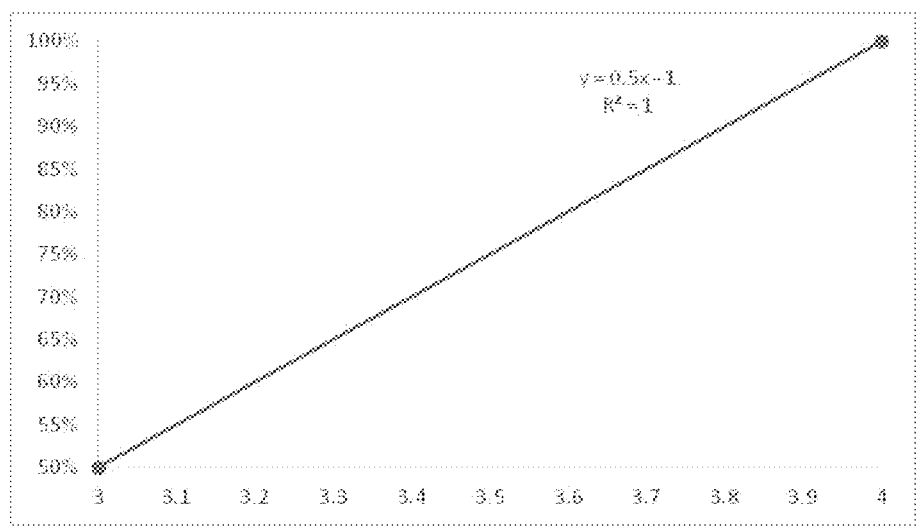

In one implementation, the corrosion degree Cij immediately after the stent is implanted is 0%. At a certain time point after the stent is implanted, when $T_1$ is equal to $T_0$ (when the image of the stent bar under the OCT does not show an arch), the corrosion degree Cij is set to be 0%. When $T_2$ is equal to $2T_0$ (the image of the stent bar under the OCT shows an arch), the corrosion degree Cij is set to be 20%. When $T_2$ is equal to $3T_0$, the corrosion degree Cij is set to be 50%. When $T_2$ is greater than or equal to $4T_0$, the corrosion degree Cij is set to be 100%. Meanwhile, in order to obtain more accurate results, a straight line is fitted between two corrosion features, and is used to summarize a part whose corrosion degree cannot be defined between the two features, so that test results are more accurate. A specific implementation method is to draw a straight line between two features. One $T_0$ is used as a reference. One $T_0$ is equal to 1; two $T_0$s are equal to 2, and the rest can be done in the same manner. By taking $T_0$ as an abscissa and taking the corrosion degree Cij as an ordinate, three straight lines are drawn respectively, as shown in FIGS. 8(a) to 8(c). The corrosion degrees Cij corresponding to the values between $T_0$ and $2T_0$, between $2T_0$ and $3T_0$, and between $3T_0$ and $4T_0$ can be directly read according to the straight lines shown in FIG. 8(a), FIG. 8(b) and FIG. 8(c) respectively or are calculated by fitting linear functions. FIG. 8(a) shows a fitted straight line of the corrosion degree Cij corresponding to $T_0$ to $2T_0$; FIG. 8(b) shows a fitted straight line of the corrosion degree Cij corresponding to $2T_0$ to $3T_0$; and FIG. 8(c) shows a fitted straight line of the corrosion degree Cij corresponding to $3T_0$ to $4T_0$.

Figure 8D:
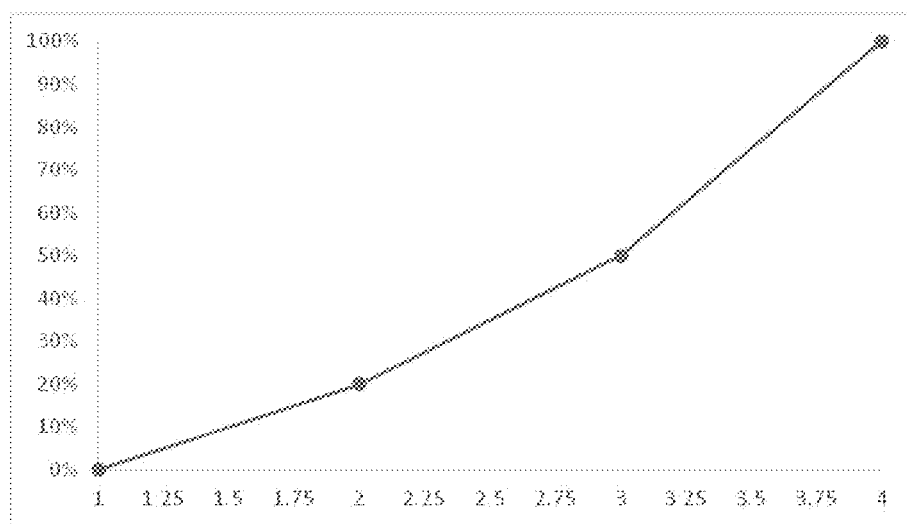

The curves shown in FIGS. 8(a) to 8(c) are summarized. As shown in FIG. 8(d), sizes of the obtained value ($T_1$ and $T_2$) in the OCT image are compared with $T_0$; and the corrosion degree Cij is directly read from the straight line shown in FIG. 8(d) or is calculated by fitting piecewise linear functions.

S50: an overall corrosion degree Cx of the absorbable stent is calculated.

A calculation formula of the overall corrosion degree C is:

$$Cx = \left( \frac{\sum_{i=1}^{n} \sum_{j=1}^{Ni} Cij}{S_0} + \frac{S_0 - S_x}{S_0} \right) \times 100\%$$

A corrosion degree of a jth stent bar rod in each frame to be analyzed is Cij.

The overall corrosion degree Cx of the absorbable stent should be an arithmetic mean value of the corrosion degrees of all stent bars from the first frame to an nth frame to be analyzed, that is:

$$Cx = \frac{\sum_{i=1}^{n} \sum_{j=1}^{Ni} Cij}{\sum_{i=1}^{n} Ni}.$$

For a metal absorbable stent, such as an iron-based alloy absorbable stent, a magnesium-based alloy absorbable stent, and a zinc-based alloy absorbable stent, after a stent bar starts to be corroded in vivo, the metal in the stent bar is continuously decomposed into ionic and solid corrosion products in vivo. The two kinds of corrosion products are eventually absorbed by a human body or metabolized out of the body under an in-vivo metabolic mechanism. In the uncorroded state, the brightness of the stent bar and the black tail shadow are relatively clear. However, when the stent bar is fully corroded, some metal corrosion products may have been transported into other tissues by surrounding tissues, resulting in the remaining metal part being fluffy, which is as dense as or is denser than the vascular wall tissue. This means that a metal part of a stent cannot be distinguished from a vascular wall tissue part in an image. As a result, some stent bars are lost in statistics, especially when $S_0$ is much greater than $S_i$, so it indicates that a large number of stent bars have been completely unrecognized during follow-up test, and these fully corroded stent bars cannot be reflected in the formula. This will cause the overall corrosion degree of the stent bars to be less than a real value.

Therefore, the above formula for calculating C needs to be compensated. Since the corrosion degree of the fully corroded stent bar is set to be 100%, on the original basis, the denominator is changed to the total number $S_0$ of the stent bars at the time zero of implantation; and on the original basis, $(S_0-S_i)*100\%$ is compensated. The formula after correction is as follows:

$$Cx = \left( \frac{\sum_{i=1}^{n} \sum_{j=1}^{Ni} Cij}{S_0} + \frac{S_0 - S_x}{S_0} \right) \times 100\%.$$

In the above-mentioned evaluation method for the corrosion degree of an absorbable stent, OCT is used for in-vivo tomography. Corrosion degrees of a plurality of stent bars are determined through OCT images, and the corrosion degrees of the plurality of stent bars are averaged and corrected to obtain a corrosion degree of the absorbable stent at a certain time after implantation. An experiment shows that the method can accurately evaluate, quantitatively or semi-quantitatively, a corrosion degree of an absorbable stent, so that the method can be applied clinically.

Figure 9:
FIG. 9 is a schematic diagram of modules of an evaluation system for the corrosion degree of an absorbable stent according to one implementation.

Further, an evaluation system for the corrosion degree of an absorbable stent is provided. As shown in FIG. 9, the evaluation system for the corrosion degree of the absorbable stent includes an OCT image obtaining module, an OCT image identification module, an OCT image analysis module and a calculation module.

The OCT image obtaining module is configured to obtain N frames of OCT images of an absorbable stent. Specifically, n frames of OCT images of the absorbable stent at the time zero of implantation and n frames of OCT images of the absorbable stent at the time x of implantation can be obtained. When the number of stent bars of the absorbable stent at the time zero of implantation is a fixed constant, n frames of OCT images of the absorbable stent at the time x of implantation may be obtained only.

In one implementation, the OCT image obtaining module collects, through an OCT catheter, images of n sections of the absorbable stent that are perpendicular to an axial central axis, i.e., the n frames of OCT images. The OCT catheter extends into a lumen, and then moves according to a set speed to collect the images of the various sections, i.e., the n frames of OCT images.

The OCT image identification module is configured to identify stent bars in each frame of OCT image, and calculate the total number Ni of the stent bars corresponding to each frame of OCT image and the total number Si of the stent bars corresponding to the n frames of OCT images, $$Sx = \sum_{i=1}^{n} Ni.$$

The stent bars (which simultaneously satisfy two conditions) are identified according to the standard above, and descriptions thereof are omitted here. The total number Ni of stent bars contained in each frame of OCT image is identified, and Nis of the n frames of OCT images are added to obtain Sx.

The OCT image analysis module is configured to analyze a corrosion degree Cij of the stent bars in each frame of OCT image. The OCT image analysis module includes a first analysis submodule and a second analysis submodule.

The working modes of the first analysis submodule and the second analysis submodule in one embodiment are as follows: The first analysis submodule is configured to identify a contour shape of each stent bar in the OCT image. When the contour is quadrilateral or crescent-shaped, it is determined that the corresponding stent bar is uncorroded or partially corroded. When the contour is roughly circular or formless, the stent bar is wrapped by a tissue, and the stent bar is internally hollowed, it is determined that the corresponding stent bar is fully corroded. When the stent bar is fully corroded, the corresponding Cij is 100%. A fully corroded stent bar is confirmed by the first analysis submodule. Further, an uncorroded stent bar and a partially corroded stent bar are distinguished by the second analysis submodule. As mentioned above, the appearance features of the uncorroded and partially corroded stent bars are quite different. The second analysis submodule can directly distinguish the uncorroded and partially corroded stent bars through image identification. Meanwhile, in order to improve the accuracy, the second analysis submodule includes a calculation and comparison secondary module configured for calculating a contour thickness of a stent bar, and for comparing the contour thickness of the stent bar with an original thickness D of the stent bar. When the calculated value of the contour thickness of the stent bar is greater than or equal to 70% D and less than or equal to 130% D, it is determined that the corrosion degree of the stent bar is no corrosion, that is, Cij=0%. When the calculated value of the contour thickness of the stent bar is greater than 130% D, it is determined that the corrosion degree of the stent bar is partial corrosion, that is, Cij=50%.

In one implementation, the calculation and comparison secondary module uses software such as Radiant to measure the contour thickness of the stent bar. It can be understood that in other implementations, the measurement is achieved not only by the Radiant software, but that any method and tool capable of measuring the contour thickness of the stent bar in the OCT image are applicable.

It should be noted that the working order of the first analysis submodule and the second analysis submodule is not limited: Both of the first analysis submodule and the second analysis submodule may work at the same time, or either one of the first analysis submodule and the second analysis submodule may start to work first.

The calculation module is configured to calculate an overall corrosion degree Cx of the absorbable stent according to a formula $$Cx = \left( \frac{\sum_{i=1}^{n}\sum_{j=1}^{Ni} Cij}{S_0} + \frac{S_0 - S_x}{S_0} \right) \times 100\%.$$

The overall corrosion degree Cx of the absorbable stent is obtained according to an output result of the calculation module.

In another embodiment, the first analysis submodule is configured to identify a contour shape of the stent bar in the OCT image. When the contour is quadrilateral or crescent-shaped or the like, the first analysis submodule determines that the corrosion degree Cij at this time is 0%. Alternatively, in order to ensure the accuracy, the second analysis submodule is further configured to calculate the contour thickness of the stent bar, and compare the contour thickness with the contour thickness $T_0$ of the stent bar at the time zero of implantation. If the calculated contour thickness is approximately equal to $T_0$, the second analysis submodule determines that the corrosion degree Cij at this time is 0%. "Approximately equal to" is determined by rounding.

When the first analysis submodule identifies that the stent bar expands into an arch structure, a radial height of the arch structure is further calculated by the second analysis submodule. When the calculated radial height is approximately equal to $2T_0$, the second analysis submodule determines that the corrosion degree Cij at this time is 20%. When the radial height is approximately equal to $3T_0$, the second analysis submodule determines that the corrosion degree Cij at this time is 50%. When the radial height is greater than or equal to $4T_0$, the second analysis submodule determines that the corrosion degree Cij at this time is 100%. When the first analysis submodule does not identify quadrilateral and crescent-shaped light spots, nor does it identify an arch region, but identifies an irregular, darker form, the first analysis submodule determines that the corrosion degree Cij at this time is 100%, or the second analysis submodule determines that the corrosion degree Cij at this time is 100%.

In another implementation, after the second analysis submodule calculates the contour thickness of the stent bar and the height of the arch, when $T_1=T_0$, $T_2=2T_0$, $T_2=3T_0$, $T_2=3T_0$ and $T_2 \geq 4T_0$, the corrosion degree Cij is determined according to the criterion mentioned above, and the corrosion degrees Cij corresponding to points within ranges from $T_0$ to $2T_0$, from $2T_0$ to $3T_0$, and from $3T_0$ to $4T_0$ are calculated according to linear functions to further improve the accuracy. The linear functions are the linear function relationships of the straight lines shown in FIGS. 8(a) to 8(d) as described above, and will not be repeated here.

The above-mentioned evaluation method for the corrosion degree of the absorbable stent and evaluation system for the corrosion degree of the absorbable stent can be applied clinically. After the absorbable stent is implanted to treat corresponding vascular disease, the above-mentioned evaluation method for the corrosion degree of the absorbable stent and evaluation system for the corrosion degree of the absorbable stent can be applied for follow-up testing, so as to evaluate the corrosion degree of the absorbable stent in vivo.

The following specific embodiments are used to verify the accuracy of the above evaluation method for the corrosion degree of the absorbable stent.

A specific experimental method is as follows:

An absorbable stent is weighed, and an original weight of the stent before implantation is recorded, assuming that the original weight is M mg. The absorbable stent is implanted in the iliofemoral artery of a rabbit (a New Zealand albino rabbit), and the corrosion degree of the absorbable stent in vivo is evaluated by the evaluation method for a corrosion degree of an absorbable stent and a weight loss method of the present disclosure.

The rabbit is implanted with the stent after anesthesia. After the stent is threaded into a 5F catheter sheath, heparin (1000 IU/mL, 150 IU/Kg) is injected. A 5F balloon catheter is inserted into a blood vessel through the catheter sheath to reach the iliac artery, and is expanded by 10-14 standard atmospheric pressures; a test stent sample is sent into the blood vessel. The blood vessel is expanded according to a ratio of the size of a balloon to the size of the blood vessel of 1:1.3; after the pressure is maintained for 30 s, a balloon conveying system is withdrawn, but the stent is left in the blood vessel.

The corrosion degree of the absorbable stent is evaluated using the evaluation method for the corrosion degree of the absorbable stent: After the implantation of the absorbable stent is completed, C7-XR Dragonfly™ equipment is used to collect multiple frames of OCT images at the time zero of implantation. After the rabbit is raised for a period of time, follow-up testing is carried out, and multiple frames of OCT images are collected at the time i of implantation; and the corrosion degree of the stent is calculated using the evaluation method for the corrosion degree of an absorbable stent. After measurement of the OCT images at the follow-up test time (the time i of implantation), the corrosion degree of the absorbable stent is measured by the weight loss method. The method is as follows: after OCT follow-up test is completed, the rabbit is killed; the stent is taken out of the body of the rabbit together with its surrounding tissue; the blood is washed away with normal saline as soon as possible. The tissue is ablated with a NaOH solution: 1 mol/L NaOH solution (which needs to immerse the top end of the stent) is added to a blood collection tube; and the blood collection tube is then put in ultrasonic cleaning equipment for ultrasonic cleaning for 20-30 min. The stent can be taken out when the endothelium is completely separated upon visual observation. The stent is put into pure water and is shook for 3-5 seconds; the stent is then taken out of the water and quickly put into absolute ethanol for shaking; finally, the stent is taken out of the absolute ethanol and put onto filter paper for drying; and after drying, the stent is put into the blood collection tube. The remaining stent bars are weighed, assuming that the stent at this time is m mg. The corrosion degree of the stent is calculated by the weight loss method.

The calculation formula of the weight loss method is: $C_{weight\ loss}=1-m/M$.

Specific embodiments are as follows:

Embodiment 1

An absorbable iron-based stent with a known original mass of 7.35 mg of the specification of 30018 (meaning that a nominal diameter after expansion was 3 mm after expansion and a nominal length was 18 mm, the same below) was implanted into the body of a rabbit, and was then removed 12 months after the implantation. According to the method above, OCT images at the time of implantation (the time zero of implantation) and at the time of follow-up test (12 months of implantation) were obtained.

When the OCT images at the time of implantation and the time of follow-up test were analyzed, all stent bars in a cross section were analyzed for every frame along a blood vessel direction, starting from the first frame where the stent bars appeared. Analysis results were as follows: a total of 45 sections were analyzed by the OCT images at the time of implantation, and the total number of stent bars in these sections was 874; a total of 45 sections were analyzed by the OCT images at the time of follow-up test, and the total number of stent bars in these sections was 789, among which, there were 425 uncorroded stent bars, 160 partially corroded stent bars, and 204 fully corroded stent bars. Therefore, the corrosion degree Cx of the stent was equal to 42.2%.

At the same time, since the residual mass of the stent after treatment was 4.56 mg, the corrosion degree $C_{weight\ loss}$ of the stent calculated by the weight loss method was equal to 38.0%.

The corrosion degree of the absorbable stent calculated by the above evaluation method for the corrosion degree of an absorbable stent is close to the corrosion degree measured by the weight loss method, indicating a smaller error in this solution.

Embodiment 2

An absorbable iron-based stent with a known original mass of 7.37 mg of the specification of 30018 was implanted into the body of a rabbit, and was then removed 18 months after the implantation. According to the method above, OCT images at the time of implantation and at the time of follow-up test were obtained.

When the OCT images at the time of implantation and the time of follow-up test were analyzed, all stent bars in a cross section were analyzed for every three frames along a blood vessel direction, starting from the first frame where the stent bars appeared. Analysis results were as follows: a total of 24 sections were analyzed by the OCT images at the time of implantation, and the total number of stent bars in these sections was 547; a total of 24 sections were analyzed by the OCT images at the time of follow-up test, and the total number of stent bars in these sections was 472, among which, there were 148 uncorroded stent bars, 165 partially corroded stent bars, and 159 fully corroded stent bars. Therefore, the corrosion degree Cx of the stent was equal to 57.8%.

At the same time, since the residual mass of the stent after treatment was 3.61 mg, the corrosion degree $C_{weight\ loss}$ of the stent calculated by the weight loss method was equal to 51.0%.

The corrosion degree of the absorbable stent calculated by the above evaluation method for the corrosion degree of an absorbable stent is close to the corrosion degree measured by the weight loss method, indicating a smaller error in this solution.

Embodiment 3

An absorbable iron-based stent with a known original mass of 7.51 mg of the specification of 30018 was implanted into the body of a rabbit, and was then removed 36 months after the implantation. According to the method above, OCT images at the time of implantation and at the time of follow-up test were obtained.

When the OCT images at the time of implantation and the time of follow-up test were analyzed, all stent bars in a cross section were analyzed in each frame along a blood vessel direction, starting from the first frame where the stent bars appeared. Analysis results were as follows: a total of 91 sections were analyzed by the OCT images at the time of implantation, and the total number of stent bars in these sections was 1760; a total of 91 sections were analyzed by the OCT images at the time of follow-up test, and the total number of stent bars in these sections was 704, among which, there were 46 uncorroded stent bars, 220 partially corroded stent bars, and 438 fully corroded stent bars. Therefore, the corrosion degree Cx of the stent segment was equal to 91.1%.

At the same time, since the residual mass of the stent after treatment was 0.83 mg, and nearly no stent bars could be found, the corrosion degree $C_{weight\ loss}$ of the stent calculated by the weight loss method was equal to 88.9%.

The corrosion degree of the absorbable stent calculated by the above evaluation method for the corrosion degree of an absorbable stent is close to the corrosion degree measured by the weight loss method, indicating a smaller error in this solution.

Embodiment 4

An absorbable zinc-based stent with a known original mass of 7.44 mg of the specification of 30018 was implanted into the body of a rabbit, and was then removed 6 months after the implantation. According to the method above, OCT images at the time of implantation and at the time of follow-up test were obtained.

When the OCT images at the time of implantation and the time of follow-up test were analyzed, all stent bars in a cross section in any one of every two frames were analyzed along a blood vessel direction, starting from the first frame where the stent bars appeared. Analysis results were as follows: a total of 46 sections were analyzed by the OCT images at the time of implantation, and the total number of stent bars in these sections was 905; a total of 46 sections were analyzed by the OCT images at the time of follow-up test, and the total number of stent bars in these sections was 852, among which, there were 779 uncorroded stent bars, 35 partially corroded stent bars, and 38 fully corroded stent bars. Therefore, the corrosion degree Cx of the stent segment was equal to 12.0%.

At the same time, since the residual mass of the stent after treatment was 6.32 mg, the corrosion degree $C_{weight\ loss}$ of the stent calculated by the weight loss method was equal to 15.1%.

The corrosion degree of the absorbable stent calculated by the above evaluation method for the corrosion degree of an absorbable stent is close to the corrosion degree measured by the weight loss method, indicating a smaller error in this solution.

Embodiment 5

An absorbable zinc-based stent with a known original mass of 7.29 mg of the specification of 30018 was implanted into the body of a rabbit, and was then removed 36 months after the implantation. According to the method above, OCT images at the time of implantation and at the time of follow-up test were obtained.

When the OCT images at the time of implantation and the time of follow-up test were analyzed, all stent bars in a cross section in any one of every four frames were analyzed along a blood vessel direction, starting from the first frame where the stent bars appeared. Analysis results were as follows: a total of 23 sections were analyzed by the OCT images at the time of implantation, and the total number of stent bars in these sections was 445; a total of 23 sections were analyzed by the OCT images at the time of follow-up test, and the total number of stent bars in these sections was 233, among which, there were 95 uncorroded stent bars, 45 partially corroded stent bars, and 103 fully corroded stent bars. Therefore, the corrosion degree Cx of the stent segment was equal to 73.6%.

At the same time, since the residual mass of the stent after treatment was 1.31 mg, the corrosion degree $C_{weight\ loss}$ of the stent calculated by the weight loss method was equal to 82.0%.

Embodiment 6

An absorbable iron-based stent with a known original mass of 7.35 mg of the specification of 30018 was implanted into the body of a rabbit, and was then removed 12 months after the implantation. According to the method above, OCT images at the time of implantation (the time zero of implantation) and at the time of follow-up test (12 months of implantation) were obtained.

When the OCT images at the time of implantation and the time of follow-up test were analyzed, all stent bars in a cross section were analyzed for every frame along a blood vessel direction, starting from the first frame where the stent bars appeared. Analysis results were as follows: a total of 45 sections were analyzed by the OCT images at the time of implantation, and the total number of stent bars in these sections was 874; a total of 45 sections were analyzed by the OCT images at the time of follow-up test, and the total number of stent bars in these sections was 789, among which, there were 390 uncorroded stent bars, 120 stent bars with a corrosion degree of 20%, 94 stent bars with a corrosion degree of 50%, and 185 fully corroded stent bars. Therefore, the corrosion degree Cx of the stent was equal to 39.0%.

At the same time, since the residual mass of the stent after treatment was 4.56 mg, the corrosion degree $C_{weight\ loss}$ of the stent calculated by the weight loss method was equal to 38.0%.

The corrosion degree of the absorbable stent calculated by the above evaluation method for the corrosion degree of an absorbable stent is close to the corrosion degree measured by the weight loss method, indicating a smaller error in this solution.

Embodiment 7

An absorbable iron-based stent with a known original mass of 7.37 mg of the specification of 30018 was implanted into the body of a rabbit, and was then removed 18 months after the implantation. According to the method above, OCT images at the time of implantation and at the time of follow-up test were obtained.

When the OCT images at the time of implantation and the time of follow-up test were analyzed, all stent bars in a cross section were analyzed for every three frames along a blood vessel direction, starting from the first frame where the stent bars appeared. Analysis results were as follows: a total of 24 sections were analyzed by the OCT images at the time of implantation, and the total number of stent bars in these sections was 547; a total of 24 sections were analyzed by the OCT images at the time of follow-up test, and the total number of stent bars in these sections was 472, among which, there were 172 uncorroded stent bars, 86 stent bars with a corrosion degree of 20%, 65 stent bars with a corrosion degree of 50%, and 149 fully corroded stent bars. Therefore, the corrosion degree Cx of the stent was equal to 50.0%.

At the same time, since the residual mass of the stent after treatment was 3.61 mg, the corrosion degree $C_{weight\ loss}$ of the stent calculated by the weight loss method was equal to 51.0%.

The corrosion degree of the absorbable stent calculated by the above evaluation method for the corrosion degree of an absorbable stent is close to the corrosion degree measured by the weight loss method, indicating a smaller error in this solution.

Embodiment 8

An absorbable iron-based stent with a known original mass of 7.51 mg of the specification of 30018 was implanted into the body of a rabbit, and was then removed 36 months after the implantation. According to the method above, OCT images at the time of implantation and at the time of follow-up test were obtained.

When the OCT images at the time of implantation and the time of follow-up test were analyzed, all stent bars in a cross section were analyzed for each frame along a blood vessel direction, starting from the first frame where the stent bars appeared. Analysis results were as follows: a total of 91 sections were analyzed by the OCT images at the time of implantation, and the total number of stent bars in these sections was 1760; a total of 91 sections were analyzed by the OCT images at the time of follow-up test, and the total number of stent bars in these sections was 704, among which, there were 35 uncorroded stent bars, 59 stent bars with a corrosion degree of 20%, 160 stent bars with a corrosion degree of 50%, and 450 fully corroded stent bars. Therefore, the corrosion degree Cx of the stent segment was equal to 90.8%.

At the same time, since the residual mass of the stent after treatment was 0.83 mg, and nearly no stent bars could be found, the corrosion degree $C_{weight\ loss}$ of the stent calculated by the weight loss method was equal to 88.9%.

The corrosion degree of the absorbable stent calculated by the above evaluation method for the corrosion degree of an absorbable stent is close to the corrosion degree measured by the weight loss method, indicating a smaller error in this solution.

Embodiment 9

An absorbable zinc-based stent with a known original mass of 7.44 mg of the specification of 30018 was implanted into the body of a rabbit, and was then removed 6 months after the implantation. According to the method above, OCT images at the time of implantation and at the time of follow-up test were obtained.

When the OCT images at the time of implantation and the time of follow-up test were analyzed, all stent bars in a cross section in any one of every two frames were analyzed along a blood vessel direction, starting from the first frame where the stent bars appeared. Analysis results were as follows: a total of 46 sections were analyzed by the OCT images at the time of implantation, and the total number of stent bars in these sections was 905; a total of 46 sections were analyzed by the OCT images at the time of follow-up test, and the total number of stent bars in these sections was 852, among which, there were 730 uncorroded stent bars, 63 stent bars with a corrosion degree of 20%, 26 stent bars with a corrosion degree of 50%, and 33 fully corroded stent bars. Therefore, the corrosion degree Cx of the stent segment was equal to 12.3%.

At the same time, since the residual mass of the stent after treatment was 6.32 mg, the corrosion degree $C_{weight\ loss}$ of the stent calculated by the weight loss method was equal to 15.1%.

The corrosion degree of the absorbable stent calculated by the above evaluation method for the corrosion degree of an absorbable stent is close to the corrosion degree measured by the weight loss method, indicating a smaller error in this solution.

Embodiment 10

An absorbable zinc-based stent with a known original mass of 7.29 mg of the specification of 30018 was implanted into the body of a rabbit, and was then removed 36 months after the implantation. According to the method above, OCT images at the time of implantation and at the time of follow-up test were obtained.

When the OCT images at the time of implantation and the time of follow-up test were analyzed, all stent bars in a cross section in any one of every four frames were analyzed along a blood vessel direction, starting from the first frame where the stent bars appeared. Analysis results were as follows: a total of 23 sections were analyzed by the OCT images at the time of implantation, and the total number of stent bars in these sections was 445; a total of 23 sections were analyzed by the OCT images at the time of follow-up test, and the total number of stent bars in these sections was 233, among which, there were 51 uncorroded stent bars, 22 stent bars with a corrosion degree of 20%, 35 stent bars with a corrosion degree of 50%, and 125 fully corroded stent bars. Therefore, the corrosion degree Cx of the stent segment was equal to 80.7%.

At the same time, since the residual mass of the stent after treatment was 1.31 mg, the corrosion degree $C_{weight\ loss}$ of the stent calculated by the weight loss method was equal to 82.0%.

The corrosion degree of the absorbable stent calculated by the above evaluation method for the corrosion degree of an absorbable stent is close to the corrosion degree measured by the weight loss method, indicating a smaller error in this solution.

Embodiment 11

An absorbable zinc-based stent with a known original mass of 7.44 mg of the specification of 30018 was implanted into the body of a rabbit, and was then removed 6 months after the implantation. According to the method above, OCT images at the time of implantation and at the time of follow-up test were obtained.

When the OCT images at the time of implantation and the time of follow-up test were analyzed, all stent bars in a cross section in any one of every two frames were analyzed along a blood vessel direction, starting from the first frame where the stent bars appeared. Analysis results were as follows: a total of 46 sections were analyzed by the OCT images at the time of implantation, and the total number of stent bars in these sections was 905; a total of 46 sections were analyzed by the OCT images at the time of follow-up test, and the total number of stent bars in these sections was 852, among which, there were 400 uncorroded stent bars ($T_1=T_0$), 15 stent bars ($T_2=2T_0$) with a corrosion degree of 20%, 19 stent bars ($T_2=3T_0$) with a corrosion degree of 50%, and 25 fully corroded stent bars ($T_2 \geq 4T_0$). For further optimization, the contour thicknesses $T_1$ of the remaining 393 stent bars in the OCT images or the radial heights $T_2$ of the arch structures are substituted into the straight lines shown in FIG. 8(a), FIG. 8(b), or FIG. 8(c), thus directly reading the corresponding Cij or calculating the Cij by means of fitting linear functions. Finally, the corrosion degree Cx of the stent segment was equal to 14.6%.

At the same time, since the residual mass of the stent after treatment was 6.32 mg, the corrosion degree $C_{weight\ loss}$ of the stent calculated by the weight loss method was equal to 15.1%.

The corrosion degree of the absorbable stent calculated by the above evaluation method for the corrosion degree of an absorbable stent is close to the corrosion degree measured by the weight loss method, indicating a smaller error in this solution.

The technical features of the embodiments described above can be arbitrarily combined. In order to make the description concise, all possible combinations of various technical features in the above embodiments are not completely described. However, the combinations of these technical features should be considered as the scope described in the present specification as long as there is no contradiction in them.

The above-mentioned embodiments only express several implementation mode's of the present invention, and their descriptions are more specific and detailed, but they cannot be understood as limiting the patent scope of the present invention. It should be noted that those of ordinary skill in the art can further make various transformations and improvements without departing from the concept of the disclosure, and these transformations and improvements all fall within the protection scope of the present invention. Therefore, the protection scope of the patent of the present invention shall be subject to the appended claims.

The invention claimed is:

1. An evaluation method for the corrosion degree of an absorbable stent, comprising the following steps:
   obtaining the total number $S_0$ of stent bars of the absorbable stent at the time zero of implantation;
   separately obtaining n frames of optical coherence tomography (OCT) images of the absorbable stent at the time x of implantation, wherein x is greater than 0, and n is a natural number greater than 1;
   determining, according to the n frames of OCT images, the total number Ni of the stent bars corresponding to each frame of OCT image, wherein i is a natural number greater than or equal to 1 and less than or equal to n; and calculating the total number Sx of the stent bars corresponding to the n frames of OCT images at the time x of implantation, $$Sx = \sum_{i=1}^{n} Ni;$$

determining a corrosion degree Cij of a jth stent bar in an ith frame of OCT image at the time x of implantation, wherein j is a natural number greater than or equal to 1 and less than or equal to Ni; and
   calculating an overall corrosion degree Cx of the absorbable stent at the time x of implantation according to the following formula:

$$Cx = \left( \frac{\sum_{i=1}^{n}\sum_{j=1}^{Ni} Cij}{S_0} + \frac{S_0 - S_x}{S_0} \right) \times 100\%.$$

2. The evaluation method for the corrosion degree of the absorbable stent according to claim 1, wherein each frame of OCT image refers to an OCT image of each section of the absorbable stent that is perpendicular to an axial central axis.

3. The evaluation method for the corrosion degree of the absorbable stent according to claim 2, wherein the absorbable stent comprises h wave loops arranged along an axial direction, with n≥h.

4. The evaluation method for the corrosion degree of the absorbable stent according to claim 2, wherein the axial distance between sections corresponding to any two adjacent frames is equal.

5. The evaluation method for the corrosion degree of the absorbable stent according to claim 1, wherein the corrosion degree Cij at least comprises no corrosion, partial corrosion and full corrosion; Cij corresponding to no corrosion is 0%; Cij corresponding to partial corrosion is 50%; and Cij corresponding to full corrosion is 100%.

6. The evaluation method for the corrosion degree of the absorbable stent according to claim 1, wherein the total number Ni of the stent bars refers to a sum of the numbers of stent bars that simultaneously satisfy the following two conditions:
   (1) in an OCT image, the brightness of a stent bar is higher than that of a surrounding tissue; and
   (2) in an OCT image, a stent bar has a black tail shadow.

7. The evaluation method for the corrosion degree of the absorbable stent according to claim 1, wherein the corrosion degree Cij at least comprises no corrosion, preliminary corrosion, partial corrosion and full corrosion; Cij corresponding to no corrosion is 0%; Cij corresponding to preliminary corrosion is 20%; Cij corresponding to partial corrosion is 50%; and Cij corresponding to full corrosion is 100%.

8. The evaluation method for the corrosion degree of the absorbable stent according to claim 7, wherein at the time zero of implantation, a contour thickness of each stent bar is $T_0$ or in a natural state, a thickness of each stent bar is $T_0$; and when the contour thickness of the stent bar is $T_1$, if $T_1$ is approximately equal to $T_0$, it is determined that the corrosion degree Cij is 0%.

9. The evaluation method for the corrosion degree of the absorbable stent according to claim 7, wherein at the time zero of implantation, a contour thickness of each stent bar is $T_0$ or in a natural state, a thickness of each stent bar is $T_0$; and when the contour of the stent bar is an arch which has a radial height of $T_2$, if $T_2$ is approximately equal to $2T_0$, it is determined that the corrosion degree Cij is 20%.

10. The evaluation method for the corrosion degree of the absorbable stent according to claim 7, wherein at the time zero of implantation, a contour thickness of each stent bar is $T_0$ or in a natural state, a thickness of each stent bar is $T_0$; and when the contour of the stent bar is an arch which has a radial height of $T_2$, if $T_2$ is approximately equal to $3T_0$, it is determined that the corrosion degree Cij is 50%.

11. The evaluation method for the corrosion degree of the absorbable stent according to claim 7, wherein at the time zero of implantation, a contour thickness of each stent bar is $T_0$ or in a natural state, a thickness of each stent bar is $T_0$; and when the contour of the stent bar is an arch which has a radial height of $T_2$, if $T_2$ is greater than or equal to $4T_0$, it is determined that the corrosion degree Cij is 100%; or, when the stent bars are irregularly connected into one piece, it is determined that the corrosion degree Cij is 100%.

12. The evaluation method for the corrosion degree of the absorbable stent according to claim 1, wherein for the absorbable stents of the same specification or for the same absorbable stent, the total number $S_0$ of the stent bars of the absorbable stent at the time zero of implantation is a constant; and the method for obtaining $S_0$ includes: obtaining n frames of OCT images of the absorbable stent at the time zero of implantation, and determining the total number $S_0$ of stent bars of the absorbable stent at the time zero of implantation according to the n frames of OCT images of the absorbable stent at the time zero of implantation.

13. An evaluation system for determining the corrosion degree of an absorbable stent, comprising:
   an OCT image obtaining module, configured to obtain n frames of OCT images of the absorbable stent;
   an OCT image identification module, configured to identify stent bars in each frame of the OCT image, and calculate the total number Ni of the stent bars corresponding to each frame of the OCT image and the total number Sx of the stent bars corresponding to the n frames of OCT images, $$Sx = \sum_{i=1}^{n} Ni;$$

an OCT image analysis module, configured to analyze a corrosion degree Cij of the stent bars in each frame of OCT image; and a calculation module, configured to calculate an overall corrosion degree Cx of the absorbable stent according to a formula $$Cx = \left( \frac{\sum_{i=1}^{n} \sum_{j=1}^{Ni} Cij}{S_0} + \frac{S_0 - S_x}{S_0} \right) \times 100\%.$$

* * * * *